US010053421B2

(12) United States Patent
Himmler et al.

(10) Patent No.: US 10,053,421 B2
(45) Date of Patent: Aug. 21, 2018

(54) METHOD FOR PRODUCING BIS(3-AMINOPHENYL)DISULFIDES AND 3-AMINOTHIOLS

(71) Applicant: BAYER CROPSCIENCE AG, Monheim (DE)

(72) Inventors: Thomas Himmler, Odenthal (DE); Julia Johanna Hahn, Duesseldorf (DE)

(73) Assignee: BAYER CROPSCIENCE AG, Monheim (DE)

( * ) Notice: Subject to any disclaimer, the term of this patent is extended or adjusted under 35 U.S.C. 154(b) by 0 days.

(21) Appl. No.: 14/651,011

(22) PCT Filed: Dec. 12, 2013

(86) PCT No.: PCT/EP2013/076301
§ 371 (c)(1),
(2) Date: Jun. 10, 2015

(87) PCT Pub. No.: WO2014/090913
PCT Pub. Date: Jun. 19, 2014

(65) Prior Publication Data
US 2015/0329485 A1    Nov. 19, 2015

(30) Foreign Application Priority Data
Dec. 12, 2012    (EP) .................................... 12196615

(51) Int. Cl.
| | | |
|---|---|---|
| *C07C 319/06* | (2006.01) | |
| *C07C 323/35* | (2006.01) | |
| *C07C 319/22* | (2006.01) | |
| *C07C 319/24* | (2006.01) | |
| *C07C 323/09* | (2006.01) | |
| *C07C 323/34* | (2006.01) | |
| *C07C 323/37* | (2006.01) | |

(52) U.S. Cl.
CPC .......... *C07C 319/06* (2013.01); *C07C 319/22* (2013.01); *C07C 319/24* (2013.01); *C07C 323/09* (2013.01); *C07C 323/34* (2013.01); *C07C 323/35* (2013.01); *C07C 323/37* (2013.01)

(58) Field of Classification Search
None
See application file for complete search history.

(56) References Cited

U.S. PATENT DOCUMENTS 2,986,581 A    5/1961 Levy et al.

FOREIGN PATENT DOCUMENTS

| | | |
|---|---|---|
| DE | 149363 A1 | 7/1981 |
| EP | 0093363 A1 | 11/1983 |
| EP | 0347370 A2 | 12/1989 |
| EP | 0416361 A1 | 3/1991 |
| EP | 0517924 A1 | 12/1992 |
| EP | 0903340 A1 | 3/1999 |
| EP | 1803712 A1 | 4/2007 |
| EP | 2143724 A1 | 1/2010 |
| EP | 2226312 A1 | 9/2010 |
| JP | 2221254 A | 4/1990 |
| JP | 4108771 A | 4/1992 |
| JP | 8198842 A | 6/1996 |
| JP | 2008308493 A | 12/2008 |
| JP | 2011219419 A | 11/2011 |
| WO | 9515954 A1 | 6/1995 |
| WO | 03060098 A2 | 7/2003 |
| WO | 2007066844 A1 | 6/2007 |
| WO | 2010031813 A1 | 3/2010 |
| WO | 2011083487 A1 | 7/2011 |
| WO | 2011141568 A1 | 11/2011 |

OTHER PUBLICATIONS

Holleman et al. Inorganic Chemistry, 2001, pp. 716-718.*
International Search Report from corresponding PCT/EP2013/076301, dated Mar. 18, 2014.
Foss et al., "Some Unsymmetrical Aryl Sulfides", Nov. 1938, vol. 60, pp. 2729-2730.
Kabalka, et al., "Synthesis of diaryl disulfides via the reductive coupling of arylsulfonyl chlorides", Elsevier, Tetrahedron Letters 50, 2009, Departments of Chemistry and Radiology, The University of Tennessee, pp. 7340-7342.

(Continued)

*Primary Examiner* — Clinton A Brooks
(74) *Attorney, Agent, or Firm* — McBee Moore Woodward & Vanik IP, LLC

(57) ABSTRACT

The present invention relates to a novel method for preparing bis(3-aminophenyl) disulphides of the general formula (I) and 3-aminothiols of the general formula (II),

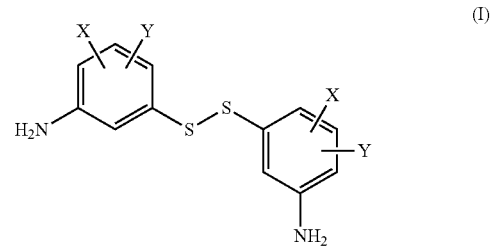

where X, Y have the meanings stated in the description, which serve as intermediates for the preparation of phenyl sulphoxides having insecticidal, acaricidal and nematicidal activity.

20 Claims, No Drawings

(56) References Cited

OTHER PUBLICATIONS

Organic Syntheses, Coll. vol. 5, p. 843, 1973; vol. 40, p. 80, 1960, 4 pages.
Robins et al., Synthesis and in vitro evaluation of 18F-labelled S-fluoroalkyl diarylguanidines: Novel high-affinity NMDA receptor antagonists for imaging with PET, Elsevier, Bioorganic & Medicinal Chemistry Letters, 20, 2010, pp. 1749-1751.
Zhang et al., "Practical and Scaleable Syntheses of 3-Hydroxythiophenol", Synthesis 2003, No. 1, Pharmaceutical and Agricultural Fine Chemicals Division, AlliedSignal Specialty Chemicals, Morristown, NJ, pp. 112-116.
Sato et al., "Preparation of bis(4-fl uoro-2-chlorophenyl) disulfidederivatives as intermediates for herbicides", Database CA, Chemical Abstracts Service, Columbus, Ohio, 1990, XP002691858.
Watanabe et al., "Preparation of diphenyl disulfides as intermediates for agrochemical microbicides", Database CA Chemical Abstracts Service, Columbus, Ohio, 996, XP002691857.
Abe et al., "(+)-I-[2,4-Dimethyl-5-(2,2,2-tri fluoroethyl sulfinyl)phenyl]-3-(trifluoromethyl )-IH-I,2,4-triazole, its preparation by optical resolution of racemate, and pesticides containing it", Database CA Chemical Abstracts Service, Columbus, Ohio, 2011, XP002691859.
Pilgram et al., "Reaction of Cyclic Phosphoramidites with Disulfides. I. A novel Synthesis of Phosphoramidothioates", Journal of Organic Chemistry, 29(7),1844-7 CODEN: JOCEAH; ISSN: 0022-3263, 964, XP002691860.
Pilgram et al., "Reaction of nitroarylthiocyanates with trialkylphosphites",Tetrahedron, 20(2), 177-87 CODEN: TETRAB; ISSN: 0040-4020, 1964, XP002691861.
Tomita et al., "Antibacterial activity of some organic compounds in vitro. V. Anti bacterial activity of diphenylethers and related compounds on *Mycobacterium tuberculosis, Staphylococcusaureus,* and *Escherichiacoli*", Yakugaku Zasshi , 72, 478-82 CODEN: YKKZAJ; ISSN: 0031-6903, 1952, XP002691862.
Sipyagin et al., "Preparation of the first ortho-substituted pentafluorosulfanylbenzenes", Journal of Fluorine Chemistry, 112(2), pp. 287-295 CODEN: J FLCAR; ISSN: 0022-1139, 2001, XP004312726.
Child, "Sulfonation of o-anisidine and aceto-o-aniside", Journal of the Chemical Society 715-20 CODEN: JCSOA9; ISSN: 0368-1769, 1932, XP002691864.
Zincke et al., "4,2-Aminotolylmercaptan", Berichte Der Deutsch En Chemischen Gesellschaft, 45, 1495-1511 CODEN: BDCGAS; ISSN: 0365-9496, 1912, XP002691865.
Hansch et al., "Catalytic synthesis of heterocycles. VIII. Dehydrocyclization of o-ethyl benzenethiols to thianaphthenes", Journal of Organic Chemistry, 21, 265-70 CODEN: JOCEAH; ISSN: 0022-3263, 1956, XP002691866.
Srisook et al., "The syntheses of 3-substituted 4-(pyridin-2-ylthio)indolesvia Leimgruber-Batchoindole synthesis", Bulletin of the Korean Chemical Society, 25 (6), 895-899 CODEN: BKCSD E; ISSN: 0253-2964, 2004, XP002721147.
Edward et al., "Notes—Synthetic Schistosomicides. I. A Diphenylsulfide Analog of Miracil D", The Journal of Organic Chemistry, Bd. 21, Nr. 12, Dec. 1, 1956 (Dec. 1, 1956), Seiten 1528-1529, XP055105480.
Bellale et al., "A simple, fast and chemoselective method for the preparation of arylthiols", Synthesis, (19), 3211-3213 CODEN: SYNTBF; ISSN: 0039-7881, 2009, XP002721148.
Database Registry Chemical Abstracts Service, Columbus, Ohio, Jun. 15, 2012 (Jun. 15, 2012), XP002721149.
Nishimura et al., "Preparation of novel catechol deri vati ves as COMT inhibitors for treatment of Parkinson's disease" Database CA Chemical Abstracts Service, Columbus, Ohio, XP002721150.
Nagata et al., "Preparation of S-(5-ami no-2-chl oro-4-fl uorobenzene)thioacetic acid methylester and its intermediate", Database CA Chemical Abstracts Service, Columbus, Ohio, XP002721151.
Wang et al., "Synthesis of "donor-bridge-acceptor" triad compounds containing the aromatic sulfurbridges", Dyes and Pigments, vol. Date 2000, 44(2), 93-100 CODEN: DYPIDX; ISSN: 0143-7208, 1999, XP002721152.

\* cited by examiner

METHOD FOR PRODUCING BIS(3-AMINOPHENYL)DISULFIDES AND 3-AMINOTHIOLS

CROSS REFERENCE TO RELATED APPLICATIONS

This application is a § 371 National Stage Application of PCT/EP2013/076301, filed 12 Dec. 2013, which claims priority to EP 12196615.4, filed 12 Dec. 2012.

BACKGROUND

Field of the Invention

The present invention relates to a novel method for preparing bis(3-aminophenyl)disulphides of the general formula (I) and 3-aminothiols of the general formula (II)

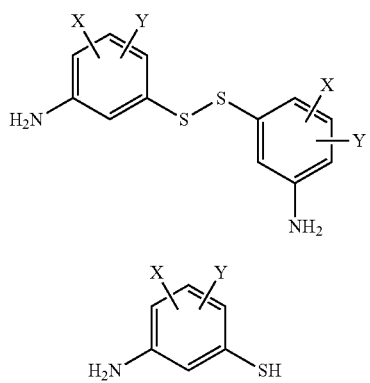

in which the residues

X and Y are each independently hydrogen, linear or branched ($C_1$-$C_4$)-alkyl, linear or branched ($C_1$-$C_4$)-alkoxy, halogen or amino.

With preference, the residues

X and Y are each independently hydrogen, linear or branched ($C_1$-$C_4$)-alkyl, halogen or amino.

With particular preference, the residues

X and Y are each independently hydrogen, methyl and ethyl, fluorine and chlorine.

Bis(3-aminophenyl)disulphides of the general formula (I) and 3-aminothiols of the general formula (II) are important intermediates for preparing agrochemical active ingredients and pharmaceutical active ingredients.

Description of Related Art

The preparation of 3-aminothiols of the general formula (II) is already known. For instance, it is possible to convert 3-nitrophenylsulphonyl chlorides of the general formula (III),

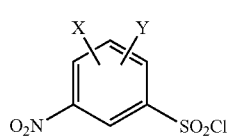

in which the residues X and Y have the meaning stated above,
to 3-aminothiols of the general formula (II), by reacting same with a large excess of a metal such as zinc (EP 2 226 312) or tin (*J. Org. Chem.* 21 (1956), 265-70) or with tin(II) chloride (*Bioorganic & Medicinal Chemistry Letters* 20 (2010) 1749-1751) in the presence of hydrochloric acid and an organic solvent.

In these reactions, in which both the nitro and the chlorosulphonyl groups are reduced in one step, large amounts of inorganic salts arise which have to be laboriously removed. This applies particularly to environmentally polluting metal salts such as zinc chloride and tin chloride. Furthermore, the chemical yields of this reduction method are not always satisfactory.

Multi-stage methods for preparing aromatic disulphides are also known, in which aromatic sulphonyl chlorides are first converted with sodium hydrogen sulphite to the sodium salts of the corresponding sulphinic acids, which are then reduced with sulphur dioxide to the diphenyl disulphides (EP 687 671; WO 2007/066844). These methods firstly require toxic gaseous sulphur dioxide and secondly do not always afford satisfactory yields. It is also known that diphenyl disulphides can be obtained starting from aromatic sulphonyl chlorides by reduction with triphenylphosphine (*Tetrahedron Letters* 50 (2009) 7340-2). Such a reduction can also be carried out by means of hydrogen bromide in a mixture of acetic acid and phenol (*J. Fluor. Chem.* 112 (2001) 287-95). These methods, however, only produce unsatisfactory yields and high amounts of waste. Most widely used is the reduction method with stoichiometric amounts of hydrogen iodide (*J. Amer. Chem. Soc.* 60 (1938) 2729-30; *Organic Syntheses, Coll. Vol.* 5(1973) 843; *Vol.* 40 (1960) 80; *Synthesis* 2003, 112-6). This method usually results in high yields but is very expensive and technically complex due to the large amounts of hydrogen iodide required and the need to dispose of, or recycle, the iodine formed.

SUMMARY

There existed, therefore, an ongoing need for a simple, economically advantageous and ecologically harmless method for reducing 3-nitrophenylsulphonyl chlorides of the general formula (III) to bis(3-aminophenyl)disulphides of the general formula (I) and 3-aminothiols of the general formula (II).

Surprisingly, this object has now been achieved by the present invention, which is characterized in that 3-nitrophenylsulphonyl chlorides of the general formula (III) are initially reduced in a first step to give bis(3-nitrophenyl) disulphides of the general formula (IV)

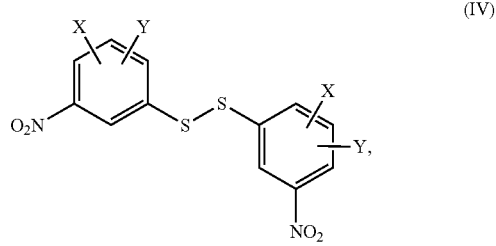

in which the residues X and Y have the meaning stated above.

These bis(3-nitrophenyl)disulphides of the general formula (IV) are then reduced in a second step in the method according to the invention to the bis(3-aminophenyl)disulphides of the general formula (I) and the 3-aminothiols of the general formula (II).

The method according to the invention is thus carried out according to reaction scheme A:

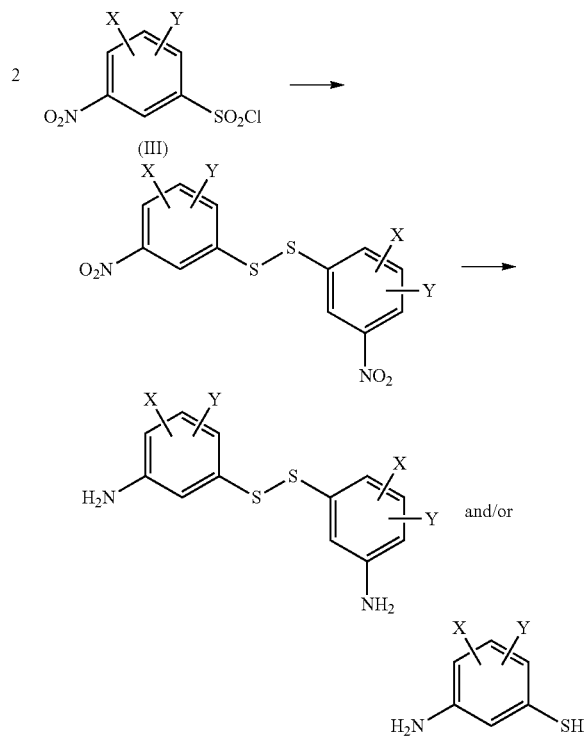

Although the method according to the invention is carried out in two stages, said method affords, surprisingly, the bis(3-aminophenyl)disulphides of the general formula (I) and the 3-aminothiols of the general formula (II) in better yields or higher purity, in comparison to the known one-stage methods, under ecologically and therefore also economically advantageous conditions.

DETAILED DESCRIPTION OF A PREFERRED EMBODIMENT

The first step of the method according to the invention is characterized in that the reduction of 3-nitrophenylsulphonyl chlorides of the general formula (III) is carried out with catalytic amounts of iodide by conducting the reaction in the presence of stoichiometric amounts of hypophosphorous acid ($H_3PO_2$) or salts thereof.

Preference is given to using hypophosphorous acid or sodium hypophosphite ($NaH_2PO_2$).

The amount of hypophosphorous acid used, or one of its salts, is 1 to 2 mol equivalents, based on the 3-nitrophenylsulfonyl chloride of the general formula (III). Preference is given to using 1.1 to 1.8 mole equivalents.

The catalyst used can be hydrogen iodide, metal iodides or elemental iodine. Preference is given to using metal iodides and elemental iodine; sodium iodide or potassium iodide are particularly preferred.

The amount of catalyst may be varied over a wide range. The smallest amount is usually taken which ensures an adequate reaction rate. In this case, the amount of catalyst is between 0.1 and 20 mol percent, based on the 3-nitrophenylsulphonyl chloride of the general formula (III). Preference is given to using 1 to 20 mol per cent.

Suitable solvents for the first step of the method according to the invention include, in principle, water and all organic solvents in which the reactants have a sufficient solubility. Examples of such organic solvents include: alcohols such as methanol, ethanol, propanol, isopropanol, butanol, isobutanol, tertiary butanol, ethylene glycol; ketones such as acetone, methyl ethyl ketone, methyl isobutyl ketone; esters such as methyl acetate and ethyl acetate; ethers such as tetrahydrofuran, 2-methyltetrahydrofuran, dioxane, methyl tertiary butyl ether; amides such as N,N-dimethylformamide and N,N-dimethylacetamide; nitriles such as acetonitrile and butyronitrile; carboxylic acids such as formic acid, acetic acid and propionic acid. It is also possible to use mixtures of these organic solvents with one another or with water.

Preference is given to using water, methanol, ethanol, propanol, isopropanol, ethylene glycol, acetone, tetrahydrofuran, N,N-dimethylformamide, acetonitrile, butyronitrile, acetic acid, propionic acid and mixtures of these solvents.

Particular preference is given to using water, methanol, ethanol, acetone, acetic acid and mixtures of these solvents. Acetic acid is especially preferred.

The temperature in the first step of the method according to the invention is between 0 and 150° C., preferably between 20 and 120° C.

The first step of the method according to the invention may also in principle be carried out under reduced or elevated pressure.

One particularly preferred embodiment of the method according to the invention is characterized in that in method step (A) nitrophenylsulphonyl chlorides of the general formula (III), in which the residues X and Y have the meaning stated above, are reduced with catalytic amounts of iodide in the presence of stoichiometric amounts of hypophosphorous acid ($H_3PO_2$) or salts thereof in an organic solvent in the presence of water to give bis(nitrophenyl)disulphides of the general formula (IV). In this embodiment, the first step of the method according to the invention is consequently carried out in an organic solvent in the presence of water.

In the reduction of nitrophenylsulphonyl chlorides of the general formula (III) to bis(nitrophenyl)disulphides of the general formula (IV), the possibility exists of an overreduction to nitrophenylthiols of the general formula (V).

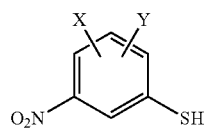

In such a case, accordingly, mixtures are then obtained consisting of the bis(nitrophenyl)disulphides of the general formula (IV) and the nitrophenylthiols of the general formula (V). This is not only disadvantageous in terms of the analytical quantification of these mixtures, but also particularly in that the nitrophenylthiols of the general formula (V), in which at least one of the residues X and Y is halogen, undergo self-condensation reactions or condensation reactions with the bis(nitrophenyl)disulphides of the general formula (IV), in which at least one of the residues X and Y is halogen, with elimination of hydrogen halide, and the secondary components thus formed may contaminate the products of the reduction of the nitrophenylsulphonyl chlorides of the general formula (III) to give bis(nitrophenyl) disulphides of the general formula (IV) and the yields achievable may be reduced. This is particularly the case if the reduction of the nitrophenylsulphonyl chlorides of the general formula (III) is carried out at relatively high concentrations of the nitrophenylsulphonyl chlorides, which is extremely desirable from an economic and ecological standpoint for achieving the highest possible space-time yields. The formation of the undesirable condensation products of the general formulae (VI) and (VII), in which the residues X and Y have the meanings stated above, may be illustrated by the following scheme:

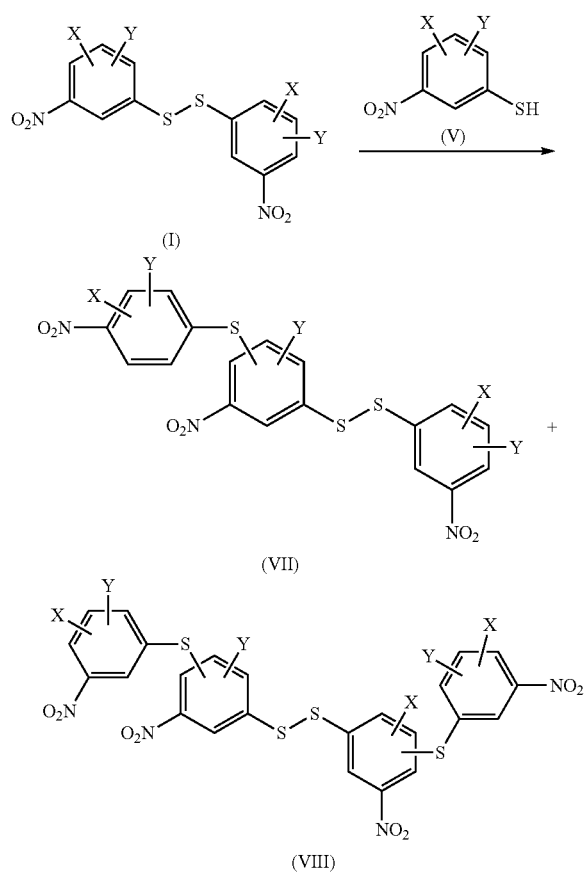

In this regard, the presence of water causes a selective reduction of the nitrophenylsulphonyl chlorides of the general formula (III) to the bis(nitrophenyl)disulphides of the general formula (IV) without forming the nitrophenylthiols of the general formula (V) and thereby also without forming undesirable condensation products of the general formulae (VI) and (VII).

Preference is given to using hypophosphorous acid or sodium hypophosphite ($NaH_2PO_2$) in the presence of water. In this case, the hypophosphorous acid may be used, for example, in its commercially available form as a 50% strength solution in water. Sodium hypophosphite ($NaH_2PO_2$) may be used as an anhydrous salt, if water is added to the solvent used. Alternatively, it is also possible to use an anhydrous solvent and to use the sodium hypophosphite in the form of its hydrate ($NaH_2PO_2 \times H_2O$).

The amount of water in this particularly preferred embodiment of the method according to the invention may be varied over a wide range and, in principle, has no upper limit, which is set at most by the solubility of the reactants in the mixture of the solvent with water. The lower limit is preferably 0.15 percent by weight, based on the sum of organic solvent and water.

In this particularly preferred embodiment of the method according to the invention, the concentration of the compound of the general formula (III) is preferably at least 0.6 mol/l and with increasing preference 0.7 mol/l, 0.8 mol/l, 0.9 mol/l, 1.0 mol/l and 1.1 mol/l.

In the second step of the method according to the invention, the bis(3-nitrophenyl)disulphides of the general formula (IV) are reduced to the bis(3-aminophenyl)disulphides of the formula (I) and the 3-aminothiols of the formula (II).

This second step of the method according to the invention is preferably carried out in a way such that the reduction is effected with hydrogen in the presence of a metal catalyst.

Useful catalysts include, firstly, noble metal catalysts having the metals ruthenium, rhodium, iridium, palladium or platinum; secondly, hydrogenation-active base metals such as nickel, cobalt, manganese, chromium or copper. The metals may generally be used in elemental form or in the form of metal salts. If the metals are used as such, they may be used either in pure form or applied to an inert support.

Preference is given to using the metals palladium, platinum, nickel and cobalt in the second step of the method according to the invention. Palladium and platinum are used here supported, for example, on activated charcoal. Nickel and cobalt are preferably used in the form of the so-called Raney metals.

The amount of catalyst may be varied over a wide range. Typically, 0.01 to 50 per cent by weight, based on the bis(3-nitrophenyl)disulphide of the general formula (IV), is used. Preference is given to using 0.01 to 5 per cent by weight of a supported palladium or platinum catalyst, and 1 to 30 per cent by weight of Raney nickel or Raney cobalt.

The heterogeneous catalysts may, in principle, also be recovered after the reaction and be re-used.

The solvent for the second step in the method according to the invention is generally an inert organic solvent. Examples here include: alcohols such as methanol, ethanol, propanol, isopropanol, butanol, isobutanol, tertiary butanol, ethylene glycol; esters such as methyl acetate and ethyl acetate; ethers such as tetrahydrofuran, 2-methyltetrahydrofuran, dioxane, methyl tertiary butyl ether; amides such as N,N-dimethylformamide and N,N-dimethylacetamide; nitriles such as acetonitrile and butyronitrile; carboxylic acids such as formic acid, acetic acid and propionic acid. It is also possible to use mixtures of these organic solvents with one another.

Preference is given to using methanol, ethanol, propanol, isopropanol, methyl acetate, ethyl acetate, tetrahydrofuran, 2-methyltetrahydrofuran, dioxane, methyl tertiary butyl ether.

The hydrogen pressure in the second step of the method according to the invention is between 1 and 150 bar, preferably between 5 and 100 bar.

The temperature in the second step of the method according to the invention is between 20 and 200° C., preferably between 20 and 150° C.

In this catalytic reduction of the bis(3-nitrophenyl)disulphides of the general formula (IV), generally mixtures of the bis(3-aminophenyl)disulphides of the general formula (I) and the 3-aminothiols of the general formula (II) are obtained. The 3-aminothiols of the general formula (II) may be converted by known methods in organic chemistry to the bis(3-aminophenyl)disulphides of the formula (I). For many purposes however, for instance for preparing alkylsulphanylbenzenes, both bis(3-aminophenyl)disulphides of the general formula (I) and 3-aminothiols of the general formula (II) may be used with equal success (*JCS Chem. Commun.* 1991, 993-4; *J. Fluor. Chem.* 105 (2000) 41-44; *Synthesis* 2007, 85-91). Purification of the mixtures of bis(3-aminophenyl)disulphides of the general formula (I) and 3-aminothiols of the general formula (II) is therefore not necessary in these cases.

The bis(3-aminophenyl)disulphides of the general formula (I) and the 3-aminothiols of the general formula (II) serve as intermediates, for example, for the preparation of phenyl sulphoxides having insecticidal, acaricidal and nematicidal activity, which are known, for example, from EP 1 803 712 and WO 2011/006605.

The present invention also relates to novel bis(3-nitrophenyl)disulphides of the general formula (IV)

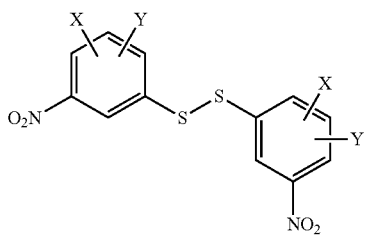
(IV)

in which the residues X and Y are each independently hydrogen, methyl, ethyl, methoxy, ethoxy, fluorine and chlorine.

With preference, the residues X and Y are each independently hydrogen, methyl, fluorine and chlorine.

The following compounds are especially preferred:
1,1'-disulphanediylbis(4-fluoro-2-methyl-5-nitrobenzene),
1,1'-disulphanediylbis(2,4-dichloro-5-nitrobenzene),
1,1'-disulphanediylbis(2-fluoro-4-methyl-5-nitrobenzene),
1,1'-disulphanediylbis(4-fluoro-2-methyl-3-nitrobenzene),
1-fluoro-4-[(4-fluoro-2-methyl-5-nitrophenyl)disulphanyl]-3-methyl-2-nitrobenzene,
1-fluoro-4-[(2-fluoro-4-methyl-5-nitrophenyl)disulphanyl]-5-methyl-2-nitrobenzene,
1-fluoro-4-[(2-fluoro-4-methyl-5-nitrophenyl)disulphanyl]-3-methyl-2-nitrobenzene.

The present invention also relates to novel 3-nitrophenylthiols of the formula (V)

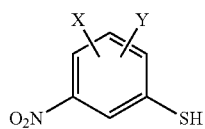
(V)

in which the residues X and Y are each independently hydrogen, methyl, ethyl, methoxy, ethoxy, fluorine and chlorine.

With preference, the residues X and Y are each independently hydrogen, methyl, fluorine and chlorine.

The following compounds are especially preferred:
4-fluoro-2-methyl-5-nitrobenzenethiol,
2,4-dimethyl-5-nitrobenzenethiol,
2,4-difluoro-5-nitrobenzenethiol,
4-chloro-2-methyl-5-nitrobenzenethiol,
2-chloro-4-methyl-5-nitrobenzenethiol,
2-fluoro-4-methyl-5-nitrobenzenethiol.

The present invention also relates to novel bis(3-aminophenyl)disulphides of the formula (I)

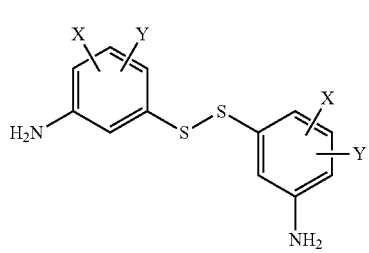
(I)

in which the residues X and Y are each independently hydrogen, methyl, ethyl, methoxy, ethoxy, fluorine and chlorine.

With preference, the residues X and Y are each independently hydrogen, methyl, fluorine and chlorine.

The following compounds are especially preferred:
3,3'-disulphanediylbis(6-fluoro-4-methylaniline),
3,3'-disulphanediylbis(4,6-dichloroaniline),
3,3'-disulphanediylbis(4-fluoro-6-methylaniline),
3,3'-disulphanediylbis(2-fluoro-6-methylaniline),
3-[(5-amino-4-fluoro-2-methylphenyl)disulphanyl]-6-fluoro-2-methylaniline,
5-[(5-amino-2-fluoro-4-methylphenyl)disulphanyl]-2-fluoro-4-methylaniline,
3-[(5-amino-2-fluoro-4-methylphenyl)disulphanyl]-6-fluoro-2-methylaniline.

The present invention also relates to novel 3-aminothiols of the general formula (II)

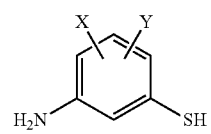
(II)

in which the residues X and Y are each independently hydrogen, methyl, ethyl, methoxy, ethoxy, fluorine and chlorine.

With preference, the residues X and Y are each independently hydrogen, methyl, fluorine and chlorine.

The following compounds are especially preferred:
5-amino-2,4-dichlorobenzenethiol,
5-amino-2-fluoro-4-methylbenzenethiol,
3-amino-2-fluoro-4-methylbenzenethiol.

The method according to the invention is illustrated by, but not restricted to, the examples below.

EXAMPLE 1

1,1'-Disulphanediylbis(4-fluoro-2-methyl-5-nitrobenzene)

3.32 g [20 mmol] of potassium iodide are added to a solution of 50.7 g [200 mmol] of 4-fluoro-2-methyl-5-nitrobenzenesulphonyl chloride in 350 ml of acetic acid and the mixture is heated to 40-45° C. At this temperature, 30.39 g [345 mmol] of sodium hypophosphite are added portionwise over the course of about 50 minutes. The mixture is stirred for 8 hours at 40-45° C., cooled to room temperature and the majority of the acetic acid is distilled off. The residue is stirred with 150 ml of water. The precipitated solid is collected under suction, washed with water and dried. 36.75 g of solid are obtained with a purity of 97.4%(w/w) (96.1% of theory).

$^1$H-NMR (600 MHz, CD$_3$CN): δ=2.50 (s, 6H), 7.34 (d, J=12.0 Hz, 2H), 8.13 (d, J=7.5 Hz, 2H) ppm.
$^{19}$F-NMR (566 MHz, CDCl$_3$): δ=−118.6 ppm.

EXAMPLE 2

1,1'-Disulphanediylbis(4-fluoro-2-methyl-5-nitrobenzene)

1.66 g [10 mmol] of potassium iodide and 10 g [75.8 mmol] of 50% aqueous hypophosphorous acid are added to a solution of 12.7 g [50 mmol] of 4-fluoro-2-methyl-5-nitrobenzenesulphonyl chloride in 100 ml of acetic acid. The mixture is heated to 60-95° C. for 6 hours, cooled to room temperature and is concentrated on a rotary evaporator. The residue is taken up in 100 ml of water and is extracted with 100 ml of ethyl acetate. The organic phase is washed with 20 ml of semiconcentrated sodium bisulphite solution, 50 ml of water and 100 ml of sodium bicarbonate solution, and is then dried and concentrated. 8.8 g of solid are obtained with a purity of 92.1% (87% of theory).

EXAMPLE 3

1,1'-Disulphanediylbis(2-fluoro-4-methyl-5-nitrobenzene)

Analogous to the procedure for example 1.
$^{19}$F-NMR (566 MHz, CDCl$_3$): δ=−101.6 ppm.

EXAMPLE 4

1,1'-Disulphanediylbis(4-fluoro-2-methyl-3-nitrobenzene)

Analogous to the procedure for example 1.
$^{19}$F-NMR (566 MHz, CDCl$_3$): δ=−122 ppm.

EXAMPLE 5

1,1'-Disulphanediylbis(2,4-dichloro-5-nitrobenzene)

Analogous to the procedure for example 1.
log P(HCOOH): 5.69; log P(neutral): 5.64
$^1$H-NMR (d-DMSO, 400 MHz) δ=8.33 (s, 2H), 8.21 (s, 2H) ppm.

EXAMPLE 6

1-Fluoro-4-[(2-fluoro-4-methyl-5-nitrophenyl)disulphanyl]-5-methyl-2-nitrobenzene Analogous to the procedure for example 1.
$^{19}$F-NMR (566 MHz, CDCl$_3$): δ=−101.6 and −118.4 ppm.

EXAMPLE 7

3,3'-Disulphanediylbis(6-fluoro-4-methylaniline)

1.96 g [5.27 mmol] of 1,1'-disulphanediylbis(4-fluoro-2-methyl-5-nitrobenzene) in 50 ml of tetrahydrofuran are hydrogenated over 0.4 g of Raney cobalt (Actimet) for 19 hours at 65° C. and 30 bar hydrogen pressure. After filtering off the catalyst, the solvent is removed on a rotary evaporator. 1.7 g of solid are obtained comprising 81.3% 3,3'-disulphanediylbis(6-fluoro-4-methylaniline) and 13.3% 5-amino-4-fluoro-2-methylbenzenethiol (97.5% of theory) by HPLC analysis.

LC/MS: 5-amino-4-fluoro-2-methylbenzenethiol: m/e=158 (MH$^+$).
3,3'-disulphanediylbis(6-fluoro-4-methylaniline): m/e=313 (MH$^+$).
GC/MS (silylated): 5-amino-4-fluoro-2-methylbenzenethiol: m/e=301 (M$^+$, 2×silyl, 50%), 286 (<5%), 181 (60%), 73 (100%).
3,3'-disulphanediylbis(6-fluoro-4-methylaniline): m/e=456 (M$^+$, 2×silyl, 100%), 441 (5%), 228 (100%), 73 (100%).
$^1$H-NMR (600 MHz, d-DMSO): δ=2.16 (s, 6H), 2.5 (m, 4H), 6.9-7 (m, 4H) ppm.
$^{19}$F-NMR (566 MHz, CDCl$_3$): δ=−134.5 ppm.

EXAMPLE 8

3,3'-Disulphanediylbis(6-fluoro-4-methylaniline)

152 g [408 mmol] of 1,1'-disulphanediylbis(4-fluoro-2-methyl-5-nitrobenzene) in 810 ml of tetrahydrofuran are hydrogenated over 16 g of Raney cobalt (Actimet) for 19 hours at 65° C. and 30 bar hydrogen pressure. After filtering off the catalyst, the solvent is removed on a rotary evaporator. 134.5 g of solid are obtained comprising 19.8% 3,3'-disulphanediylbis(6-fluoro-4-methylaniline) and 75.1% 5-amino-4-fluoro-2-methylbenzenethiol (99.6% of theory) by HPLC analysis.

EXAMPLE 9

3,3'-Disulphanediylbis(6-fluoro-4-methylaniline)

2.91 g [7.8 mmol] of 1,1'-disulphanediylbis(4-fluoro-2-methyl-5-nitrobenzene) in 35 ml of tetrahydrofuran are hydrogenated over 0.3 g of Raney nickel (A 4000) for 19 hours at 65° C. and 30 bar hydrogen pressure. After filtering off the catalyst, the solvent is removed on a rotary evaporator. 2.6 g of solid are obtained comprising 67.3% 3,3'-disulphanediylbis(6-fluoro-4-methylaniline) and 12.6% 5-amino-4-fluoro-2-methylbenzenethiol (85% of theory) by HPLC analysis.

EXAMPLE 10

3,3'-Disulphanediylbis(6-fluoro-4-methylaniline)

34.2 g [91.8 mmol] of 1,1'-disulphanediylbis(4-fluoro-2-methyl-5-nitrobenzene) in 180 ml of methyl tertiary butyl ether are hydrogenated over 1.8 g of Raney cobalt (Actimet) for 19 hours at 65° C. and 30 bar hydrogen pressure. After filtering off the catalyst, the solvent is removed on a rotary evaporator. 29.7 g of solid are obtained comprising 8.3% 3,3'-disulphanediylbis(6-fluoro-4-methylaniline) and 89.5% 5-amino-4-fluoro-2-methylbenzenethiol (92% of theory) by HPLC analysis.

EXAMPLE 11

3,3'-Disulphanediylbis(6-fluoro-4-methylaniline)

34.2 g [91.8 mmol] of 1,1'-disulphanediylbis(4-fluoro-2-methyl-5-nitrobenzene) in 180 ml of acetic acid are hydrogenated over 1.8 g of Raney cobalt (Actimet) for 19 hours at 65° C. and 30 bar hydrogen pressure. After filtering off the catalyst, the solvent is removed on a rotary evaporator. 30.1 g of solid are obtained comprising 8.9% 3,3'-disulphanediylbis(6-fluoro-4-methylaniline) and 89.3% 5-amino-4-fluoro-2-methylbenzenethiol by HPLC analysis.

EXAMPLE 12

3,3'-Disulphanediylbis(6-fluoro-4-methylaniline)

34.2 g [91.8 mmol] of 1,1'-disulphanediylbis(4-fluoro-2-methyl-5-nitrobenzene) in 180 ml of isobutyl alcohol are hydrogenated over 1.8 g of Raney cobalt (Actimet) for 19 hours at 65° C. and 30 bar hydrogen pressure. After filtering off the catalyst, the solvent is removed on a rotary evaporator. 30 g of solid are obtained comprising 16% 3,3'-disulphanediylbis(6-fluoro-4-methylaniline) and 80.7% 5-amino-4-fluoro-2-methylbenzenethiol by HPLC analysis.

EXAMPLE 13

3,3'-Disulphanediylbis(6-fluoro-4-methylaniline)

0.97 g [2.6 mmol] of 1,1'-disulphanediylbis(4-fluoro-2-methyl-5-nitrobenzene) in 9 ml of tetrahydrofuran is hydrogenated over 44 mg of 5% Pt/C (Evonik F 105 NC/W) for 19 hours at 65° C. and 60 bar hydrogen pressure. After filtering off the catalyst, the solvent is removed on a rotary evaporator. 0.87 g of solid is obtained comprising 8% 3,3'-disulphanediylbis(6-fluoro-4-methylaniline) and 88.3% 5-amino-4-fluoro-2-methylbenzenethiol by HPLC analysis.

EXAMPLE 14

3,3'-Disulphanediylbis(4,6-dichloroaniline)

Analogous to the procedure for example 9.
log P(HCOOH): 5.14; log P (neutral): 4.95
$^1$H-NMR (d-DMSO, 400 MHz) δ=7.41 (s, 2H), 6.95 (s, 2H), 5.78 (broad, 4H) ppm.
GC-MS: EI-Mass (m/z): 386 (4 Cl) [M]$^+$ The examples and comparative examples below relate to configurations of method step (A) of the method according to the invention. The product preferably obtained is therefore a bis(3-nitrophenyl)disulphide of the general formula (IV).

EXAMPLE 15

1,1'-Disulphanediylbis(4-fluoro-2-methyl-5-nitrobenzene)

1.66 g [10 mmol] of potassium iodide are added to a solution of 25.4 g [100 mmol] of 4-fluoro-2-methyl-5-nitrobenzenesulphonyl chloride in 50 g (47.7 ml) of acetic acid and the mixture is heated to 60° C. At this temperature, 15.9 g [150 mmol] of sodium hypophosphite monohydrate (corresponds to 2.7 g of water or 5.1% by weight) are added portionwise over the course of about 100 minutes. The mixture is stirred for 6 hours at 60-62° C., cooled to 40° C., 50 ml of water are added thereto and the mixture is stirred for 30 minutes at 40° C. The mixture is then cooled to 10° C., the precipitated solid is filtered off, washed with 60 ml of ice water and dried. 16.99 g of solid are obtained.

HPLC analysis: 92.9 area % (IV), <0.1 area % (V); <0.1 area % (VI), <0.1 area % (VII)
Yield: 85% of theory.
$^1$H-NMR (600 MHz, CD$_3$CN): δ=2.50 (s, 6H), 7.34 (d, J=12.0 Hz, 2H), 8.13 (d, J=7.5 Hz, 2H) ppm.
$^{19}$F-NMR (566 MHz, CDCl$_3$): δ=−118.6 ppm.

EXAMPLE 16

1,1'-Disulphanediylbis(4-fluoro-2-methyl-5-nitrobenzene)

1.66 g [10 mmol] of potassium iodide are added to a solution of 25.4 g [100 mmol] of 4-fluoro-2-methyl-5-nitrobenzenesulphonyl chloride in 50 g (47.7 ml) of acetic acid and 0.54 g of water (corresponds to 1.07% by weight) and the mixture is heated to 60° C. At this temperature, 13.2 g [150 mmol] of sodium hypophosphite having a water content of about 0.4% are added portionwise over the course of about 100 minutes. The mixture is stirred for 6 hours at 60-62° C., cooled to 40° C., 50 ml of water are added thereto and the mixture is stirred for 30 minutes at 40° C. The mixture is then cooled to 10° C., the precipitated solid is filtered off, washed with 60 ml of ice water and dried. 17.34 g of solid are obtained.

HPLC analysis: 91.6 area % (IV), <0.1 area % (V); <0.1 area % (VI), <0.1 area % (VII)
Yield: 85% of theory.

COMPARATIVE EXAMPLE 1

1,1'-Disulphanediylbis(4-fluoro-2-methyl-5-nitrobenzene)

1.66 g [10 mmol] of potassium iodide are added to a solution of 25.4 g [100 mmol] of 4-fluoro-2-methyl-5-nitrobenzenesulphonyl chloride in 50 g (47.7 ml) of acetic acid and the mixture is heated to 60° C. At this temperature, 13.2 g [150 mmol] of anhydrous sodium hypophosphite having a water content of about 0.4% are added portionwise over the course of about 100 minutes. The mixture is stirred for 6 hours at 60-62° C., cooled to 40° C., 50 ml of water are added thereto and the mixture is stirred for 30 minutes at 40° C. The mixture is then cooled to 10° C., the precipitated solid is filtered off, washed with 60 ml of ice water and dried. 17.14 g of solid are obtained.

HPLC analysis: 8.7 area % (IV), 83.7 area % (V); 2.2 area % (VI), 0.3 area % (VII)
Yield: 8% of theory of (IV), 74.6% of theory of (V).

EXAMPLE 17

1,1'-Disulphanediylbis(4-fluoro-2-methyl-5-nitrobenzene)

1.66 g [10 mmol] of potassium iodide are added to a solution of 25.4 g [100 mmol] of 4-fluoro-2-methyl-5-nitrobenzenesulphonyl chloride in 96.5 g (92 ml) of acetic acid and 3 g of water (corresponds to 3.0% by weight) and the mixture is heated to 60° C. At this temperature, 13.2 g [150 mmol] of anhydrous sodium hypophosphite are added portionwise over the course of about 100 minutes. The mixture is stirred for 5 hours at 58-62° C., cooled to 40° C., 50 ml of water are added thereto and the mixture is stirred for 30 minutes at 40° C. The mixture is then cooled to 10° C., the precipitated solid is filtered off, washed with 60 ml of ice water and dried. 16.54 g of solid are obtained.

HPLC analysis: 92.9 area % (IV), <0.1 area % (V); <0.1 area % (VI), <0.1 area % (VII)
Yield: 83% of theory.

EXAMPLE 18

1,1'-Disulphanediylbis(4-fluoro-2-methyl-5-nitrobenzene)

Procedure as in example 17, but using 98.1 g (93.5 ml) of acetic acid and 1.5 g of water (corresponds to 1.5% by weight). 16.91 g of solid are obtained.

HPLC analysis: 92.1 area % (IV), <0.1 area % (V); <0.1 area % (VI), <0.1 area % (VII)

Yield: 84% of theory.

EXAMPLE 19

1,1'-Disulphanediylbis(4-fluoro-2-methyl-5-nitrobenzene)

Procedure as in example 17, but using 98.85 g (94.2 ml) of acetic acid and 0.75 g of water (corresponds to 0.38% by weight). 17.31 g of solid are obtained.

HPLC analysis: 90.9 area % (IV), <0.1 area % (V); <0.1 area % (VI), <0.1 area % (VII)

Yield: 84% of theory.

EXAMPLE 20

1,1'-Disulphanediylbis(4-fluoro-2-methyl-5-nitrobenzene)

Procedure as in example 17, but using 99.2 g (94.6 ml) of acetic acid and 0.375 g of water (corresponds to 0.38% by weight). 17.20 g of solid are obtained.

HPLC analysis: 92 area % (IV), <0.1 area % (V); <0.1 area % (VI), <0.1 area % (VII)

Yield: 86% of theory.

EXAMPLE 21

1,1'-Disulphanediylbis(4-fluoro-2-methyl-5-nitrobenzene)

Procedure as in example 17, but using 99.4 g (94.8 ml) of acetic acid and 0.188 g of water (corresponds to 0.19% by weight). 16.97 g of solid are obtained.

HPLC analysis: 94.6 area % (IV), <0.1 area % (V); <0.1 area % (VI), <0.1 area % (VII)

Yield: 86% of theory.

COMPARATIVE EXAMPLE 2

1,1'-Disulphanediylbis(4-fluoro-2-methyl-5-nitrobenzene)

Procedure as in example 17, but using 99.5 g (94.9 ml) of acetic acid and 0.094 g of water (corresponds to 0.09% by weight). 16.37 g of solid are obtained.

HPLC analysis: 37.8 area % (IV), 49.5 area % (V); 8.7 area % (VI), 0.9 area % (VII)

Yield: 33.2% of theory of (IV), 43.3% of theory of (V).

COMPARATIVE EXAMPLE 3

1,1'-Disulphanediylbis(4-fluoro-2-methyl-5-nitrobenzene)

Procedure as in example 17, but using 100 g (95.3 ml) of acetic acid without addition of water. 15.96 g of solid are obtained.

HPLC analysis: 5.0 area % (IV), 89.3 area % (V); 2.2 area % (VI), 0.4 area % (VII)

Yield: 4.3% of theory of (IV), 75.8% of theory of (V).

The invention claimed is:

1. A method for preparing a bis(3-aminophenyl) disulphide of formula (I) and/or a 3-aminothiol of formula (II)

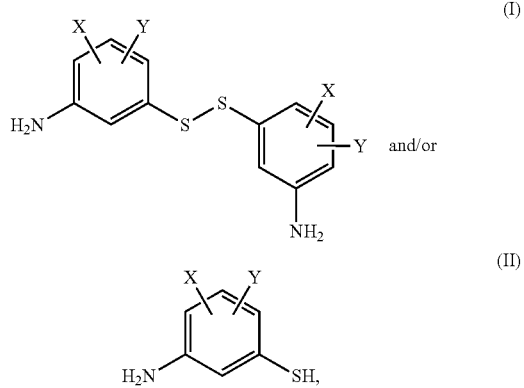

where the residues X and Y are each independently hydrogen, linear or branched ($C_1$-$C_4$)-alkyl, linear or branched ($C_1$-$C_4$)-alkoxy, halogen or amino;

comprising (A) reducing a 3-nitrophenylsulphonyl chloride of formula (III)

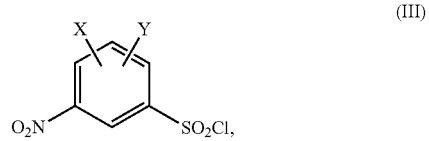

where the residues X and Y have the meanings stated above, with a catalyst consisting of catalytic amount of iodide in the presence of hypophosphorous acid ($H_3PO_2$) and/or a salt thereof to give a bis(3-nitrophenyl) disulphide of formula (IV)

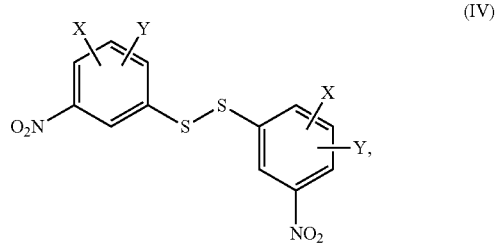

in which the residues X and Y have the meaning stated above, and (B) reducing said compound of formula (IV) with a reducing agent consisting of hydrogen in the presence of one or more metal catalysts selected from the group consisting of palladium, platinum, nickel, and cobalt, to form the bis(3-aminophenyl) disulphide of formula (I) and/or 3-aminothiol of formula (II).

2. The method according to claim 1, wherein a catalytic amount of metal iodide is used in (A), where the amount of catalyst is between 0.1 and 20 mol percent, based on the compound of formula (III).

3. The method according to claim 1, wherein 1 to 2 mole equivalents of hypophosphorous acid or sodium hypophosphite are used in (A), based on the compound of formula (III).

4. The method according to claim 1, wherein the amount of metal catalyst used in (B) is 0.01 to 50 per cent by weight, based on the compound of formula (IV).

5. The method according to claim 1, wherein the temperature in (B) is between 20° and 150° C.

6. The method according to claim 1, wherein the temperature in (A) is between 0° and 150° C.

7. The method according to claim 1, wherein (A) is carried out in an organic solvent in the presence of water.

8. The method according to claim 7, wherein hypophosphorous acid or sodium hypophosphite ($NaH_2PO_2$) is used in the presence of water.

9. The method according to claim 7, wherein the amount of water is at least 0.15 percent by weight, based on the sum of organic solvent and water.

10. The method according to claim 7, wherein the water is provided by sodium hypophosphite in the form of a hydrate ($NaH_2PO_2 \times H_2O$) thereof.

11. The method according to claim 7, wherein the concentration of the compound of formula (III) is at least 0.6 mol/l.

12. The method according to claim 1, wherein the 3-nitrophenylsulphonyl chloride of formula (III) is 4-fluoro-2-methyl-5-nitrobenzenesulphonyl chloride.

13. The method according to claim 1, wherein a bis(3-aminophenyl) disulphide of formula (I) is prepared.

14. The method according to claim 1, wherein a 3-aminothiol of formula (II) is prepared.

15. The method according to claim 1, wherein the residues X and Y are each independently hydrogen, methyl, ethyl, methoxy, ethoxy, fluorine or chlorine.

16. The method according to claim 1, wherein X or Y or both are independently a halogen.

17. The method according to claim 1, wherein X or Y or both are amino.

18. The method according to claim 1, wherein X or Y or both are independently a linear or branched ($C_1$-$C_4$)-alkyl.

19. The method according to claim 1, wherein X or Y or both are independently a linear or branched ($C_1$-$C_4$)-alkoxy.

20. The method according to claim 1, wherein X is fluorine and Y is methyl.

* * * * *